United States Patent [19]

Della-Bella et al.

[11] 4,056,634
[45] Nov. 1, 1977

[54] DIMERCAPTOETHYL ETHER SULFONIUM COMPOUNDS AND USE AS ANTIINFLAMMATORY AND ANTIRHEUMATIC AGENTS

[75] Inventors: Davide Della-Bella, Milan; Dario Chiarino, Monza, Milan, both of Italy

[73] Assignee: Whitefin Holding S.A., Lugano, Switzerland

[21] Appl. No.: 658,756

[22] Filed: Feb. 17, 1976

[30] Foreign Application Priority Data

Feb. 19, 1975  Italy .................................. 20419/75

[51] Int. Cl.² ..................... C01B 33/12; C07C 149/46
[52] U.S. Cl. ................................. 424/335; 260/607 B
[58] Field of Search .................... 260/607 B; 424/335

[56] References Cited

U.S. PATENT DOCUMENTS 2,230,587  2/1941  Chwala et al. .................. 260/607 B

FOREIGN PATENT DOCUMENTS 2,130,775  6/1971  Germany ............................ 424/335

OTHER PUBLICATIONS

Derwent Japanese Patents Report 6, No. 38, pp. 2, 3, (1967).

Primary Examiner—Delbert R. Phillips
Attorney, Agent, or Firm—Stevens, Davis, Miller & Mosher

[57] ABSTRACT

The present invention relates to a new dimercaptoethylether derivative, namely 2,2'-bis(dimethylsulfoniumethyl)ether diiodide of the formula

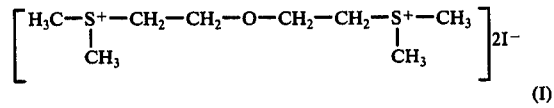

(I)

prepared by reacting the 2,2'-bis(methylmercaptoethyl)ether of the formula

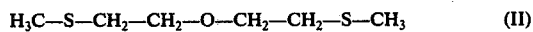

(II)

with methyl iodide.

1 Claim, No Drawings

DIMERCAPTOETHYL ETHER SULFONIUM COMPOUNDS AND USE AS ANTIINFLAMMATORY AND ANTIRHEUMATIC AGENTS

The present invention relates to a new therapeutically useful compound and to the process for the preparation thereof.

More particularly the present invention relates to a new dimercaptoethylether derivative, namely 2,2'-bis(-dimethylsulfoniumethyl)ether diiodide of the formula

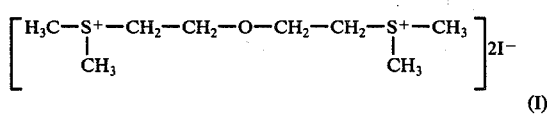

(I)

The new compound is prepared by reacting the 2,2'-bis(methylmercaptoethyl)ether of the formula $$H_3C-S-CH_2-CH_2-O-CH_2-CH_2-S-CH_3 \quad (II)$$

with methyl iodide. The reaction is preferably carried out at room temperature, in a polar organic solvent, such as acetone or alcohols. The reaction times may widely vary according to the solvent used; however, under the optimum conditions the reaction can be completed within 15 minutes.

The starting product (II) is a new compound. Therefore it is an object of the present invention both as such and as useful intermediate for preparing a new compound active both in human and veterinary therapy. The compound (II) can be prepared according to one of the known methods for preparing ethers and thioethers. Particularly high yields, even more than 90%, are obtained by the following methods:

a.

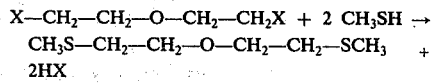

wherein X is a halogen atom.

The process is preferably carried out in the presence of alkali hydroxide, by using a water and alcohols mixture as solvent, at a temperature comprised between the room temperature and the boiling temperature of the reaction mixture.

The methylmercaptane is used in a slight excess of the stoichiometric amount in respect to 2,2'-bis(chloroethyl)ether. The reaction product is separated by distillation.

b. Methylation of 2,2'-(mercaptoethyl)ether of the formula

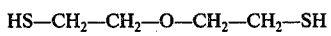

The methylation can be carried out by methyl sulphate or methyl halide, in the presence of alkalies, by operating in an alcoholic medium, at a temperature comprised between the room temperature and the boiling temperature of the reaction mixture.

The reaction product is separated by fractional distillation. The new compound according to the present invention is endowed with antiinflammatory and antirheumatic activity and can be administed in admixture with binding agents, solvents, diluents and excipients commonly used in the pharmaceutical industry for preparing capsules, tablets, syrups, vials and the other pharmaceutical forms useful for the oral or parenteral administration, both for human and veterinary use.

The antiinflammatory and antirheumatic activity has been evidenced in the rat in comparison with known drugs, such as acetylsalicylic acid and phenylbutazone.

The evaluation of the pharmacological activity of the compound of the present invention in comparison with known drugs, has been effected by using equiactive doses or doses equidistant from the corresponding lethal toxic doses obtained under the same experimental conditions (animal strains and administration mode) under which the activity test was carried out.

Namely, the antiinflammatory activity has been evidenced by the "Granuloma pouch" test (Selye - Proc.-Soc.exp.Biol.Med. 82, 328, 1953) by daily oral administrations of doses equal to 1/17 of the corresponding $DL_{50}$.

The data obtained are reported in Table 1 wherein the compound of the present invention namely

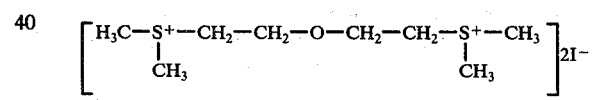

is identified as Z.964.

TABLE 1

| | | | | | Pouch wall | | | |
| | | | | | Fresh weight (g) | | Fresh weight (g) | |
| Groups N = 10 | Dose mg/Kg/os | Dose $LD_{50}$ | Exudate volume (ml) $\bar{x} \pm$ s.e. (1) | % inhib. | $\bar{x} \pm$ s.e. (1) | % inhib. | $\bar{x} \pm$ s.e. (1) | % inhib. |
|---|---|---|---|---|---|---|---|---|
| Controls | — | — | 13.2 ± 2.19 | — | 5.10 ± 0.53 | — | 1126.7 ± 156.7 | — |
| Z.964 | 300 | 0.06 | 6.15 ± 0.69 | 53* | 2.70 ± 0.27 | 48 | 708.9 ± 79.0 | 38* |
| Phenylbutazone | 80 | 0.06 | 9.70 ± 1.65 | 28 n.s. (2) | 3.72 ± 0.28 | 27 | 916.0 ± 67.2 | 20 n.s. (2) |

*P<0.05
(1) s.e. = standard error
(2) n.s. = not significant

The influence of the new compound on arthritis has been on the contrary evidenced by the Freund's adjuvant arthritis test in rats according to the experimental Perper's design (Perper R. J. et. al.: Proc.Soc.exp.Biol.Med. 137, 506, 1971) by daily oral administrations of doses corresponding to 1/25 of the lethal toxic doses.

The thus obtained results are reported in Table 2.

TABLE 2

| Groups N = 10 | Dose mg/Kg/os | Dose LD$_{50}$ | ΔVolume (ml) (injected paw) | | ΔVolume (ml) (not injected paw; opposite site) | |
|---|---|---|---|---|---|---|
| | | | $\bar{x} \pm$ s.e. | % inhib. | $\bar{x} \pm$ s.e. | % inhib. |
| Arthritic controls | — | — | 3.21 ± 0.27 | — | 1.68 ± 0.14 | — |
| Z.964 | 200 | 0.04 | 2.17 ± 0.24 | 32 | 0.61 ± 0.13 | 63 |
| Phenylbutazone | 50 | 0.04 | 2.97 ± 0.14 | 8 | 1.74 ± 0.13 | 0 |

Finally, as far as toxicological toxicological aspect is concerned, the experimental data of DL$_{50}$ obtained in rats by intraperitoneal and oral administrations of the compound according to the present invention, in comparison with acetylsalicylic acid and phenylbutazone, are reported in Table 3.

TABLE 3

| Drugs | LD$_{50}$ mg/Kg | |
|---|---|---|
| Z.064 | 1150 | intraperitoneally |
| Z.964 | >5000 | Orally |
| Phenylbutazone | 215 | intraperitoneally |
| Phenylbutazone | 1280 | Orally |
| Acetylsalicylic acid | 500 | Intraperitoneally |
| Acetylsalicylic acid | 1500 | Orally |

The following examples relating to the preparation of the compound of the present invention are given by way of illustration only, and they are not in anyway limitative.

EXAMPLE 1

33.25 g (1.445 mols) of sodium were dissolved into 600 ml of absolute ethyl alcohol.

The thus obtained solution was added dropwise to 100.00 g (0.72 mol) of 2,2'-(mercaptoethyl)ether under stirring and the whole was heated under reflux for 1 hr.

The thus prepared solution was added dropwise and under stirring to 89.20 g (0.707 mol) of dimethylsulphate and the whole was heated under stirring and reflux overnight. The solution was then evaporated to dryness and extracted with ethyl ether; the extract was washed with water, and dried over anhydrous sodium sulphate.

After removing the ether by evaporation the oily residue was purified by fractional distillation.

102.2 g (85% yield on theoretical) of 2,2'-bis(methylmercaptoethyl) ether was obtained.

B.P. 105°–107° C/7.5 mmHg.

Analysis: Calcd. for C$_6$H$_{14}$OS$_2$ : S 38.56%. Found: S 38.21%.

37.00 g (0.222 mol) of acetone solution of 2,2'-bis(methylmercaptoethyl) ether prepared as above described, were added dropwise and under stirring to 69.00 g (0.486 mol) of methyliodide. The stirring was continued for about 20 hrs at room temperature.

The whole was then diluted with acetone and filtered off; the precipitate was washed with acetone, crystallized from methanol and dried under vacuum at room temperature.

90 g of 2,2'-bis(dimethylsulphoniumethyl)ether diiodide were obtained.

M.P. 144°–146° C (yield 90% on theoretical).

Analysis: Calcd. for C$_8$H$_{20}$OS$_2$I$_2$ : S 14.25% I 55.38%. Found: S 14.19% I 56.14%.

EXAMPLE 2

A stream of CH$_3$SH (215 g corresponding to 4.46 mols) was bubbled under stirring into a solution of g 175 (4.37 mols) of sodium hydroxide drops (99%) in 200 ml water and 3,000 ml ethanol, by keeping the temperature of the solution at 30°–40° C.

The thus obtained solution was added dropwise and under stirring to 280 g (1.96 mols) of 2,2'-bis(chloroethyl)ether, by keeping the temperature at about 30° C.

The whole was refluxed for 18 hrs; after removing the solvent by distillation, the residue was treated with ether, the ethereal extract was dried on anhydrous Na$_2$SO$_4$ and the solvent removed by evaporation. The oily residue was purified by fractional distillation.

297.5 g (91.5% yield on theoretical) of 2,2'-bis(methylmercaptoethyl) ether were obtained; B.P. 80°–2° C/1.5 mmHg.

Analysis: Calcd. for C$_6$H$_{14}$OS$_2$ : S 38.56%. Found: S 38.28%. 37.00 g (0.222 mol) acetone solution of 2,2'-bis(methylmercaptoethyl) ether was added dropwise and under stirring to 69.00 g (0.486 mol) of methyl iodide. The stirring was continued for about 20 hrs by keeping at room temperature. The solution was then diluted with acetone and filtered off; after washing with acetone the precipitate was crystallized from methanol and dried under vacuum at room temperature.

90 g of 2,2'-bis(dimethylsulphoniumethyl)ether diiodide were obtained.

M.P. 144°–146° C (90% yield on theoretical).

Analysis: Calcd. for C$_8$H$_{20}$OS$_2$I$_2$ : S 14.25% I 56.38%. Found: S 14.19% I 56.14%.

We claim:

1. Pharmaceutical compositions having antiinflammatory and antirheumatic activity, containing a therapeutically effective amount of the compound of formula

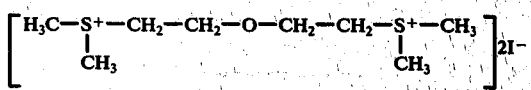

in admixture with suitable binding agents, excipients, diluents as well as carriers therapeutically acceptable for human and veterinary use.

* * * * *